United States Patent
Vicario et al.

(10) Patent No.: US 11,678,815 B2
(45) Date of Patent: Jun. 20, 2023

(54) OXYGEN CONSUMPTION DETERMINATION

(71) Applicant: KONINKLIJKE PHILIPS N.V., Eindhoven (NL)

(72) Inventors: Francesco Vicario, Boston, MA (US); Roberto Buizza, Malden, MA (US)

(73) Assignee: Koninklijke Philips N.V., Eindhoven (NL)

(*) Notice: Subject to any disclaimer, the term of this patent is extended or adjusted under 35 U.S.C. 154(b) by 333 days.

(21) Appl. No.: 17/094,170

(22) Filed: Nov. 10, 2020

(65) Prior Publication Data

US 2021/0236757 A1    Aug. 5, 2021

Related U.S. Application Data

(60) Provisional application No. 62/968,197, filed on Jan. 31, 2020.

(51) Int. Cl.
*A61B 5/083* (2006.01)
*A61M 16/08* (2006.01)
(Continued)

(52) U.S. Cl.
CPC ............ *A61B 5/0833* (2013.01); *A61B 5/097* (2013.01); *A61M 16/024* (2017.08); *A61M 16/026* (2017.08); *A61M 16/085* (2014.02); *A61M 16/0057* (2013.01); *A61M 2016/0039* (2013.01); *A61M 2016/0042* (2013.01);
(Continued)

(58) Field of Classification Search
CPC ..... A61B 5/0833; A61B 5/0836; A61B 5/087; A61B 5/097; A61M 16/00; A61M 16/0057; A61M 16/024; A61M 2016/0033; A61M 2016/0036; A61M 2016/0039; A61M 2016/0042; A61M 2016/1025; A61M 2202/0208; A61M 2230/435
See application file for complete search history.

(56) References Cited

U.S. PATENT DOCUMENTS 6,450,968 B1   9/2002   Castor et al.
6,581,595 B1   6/2003   Murdock
(Continued)

FOREIGN PATENT DOCUMENTS

JP    2004041247 A   *   2/2004
WO    2017079425 A1       5/2017
(Continued)

OTHER PUBLICATIONS

Machine translation of JP-2004041247-A.*
(Continued)

*Primary Examiner* — Joseph D. Boecker
(74) *Attorney, Agent, or Firm* — Daniel H. Brean; Andrew M. Gabriel

(57) ABSTRACT

A computer-implemented method is described. The method includes receiving an indication and determining a subject's oxygen consumption based on the indication. The indication refers to an oxygen fraction in a sample of inhalation gas delivered by a ventilator for inhalation by a subject. The indication further refers to an oxygen fraction in a sample of exhalation gas exhaled by the subject. The indication further refers a measurement of a flow rate of the exhalation gas.

15 Claims, 4 Drawing Sheets

(51) Int. Cl.
*A61M 16/00* (2006.01)
*A61M 16/10* (2006.01)
*A61B 5/097* (2006.01)

(52) U.S. Cl.
CPC .............. *A61M 2016/1025* (2013.01); *A61M 2202/0208* (2013.01); *A61M 2202/0225* (2013.01); *A61M 2230/435* (2013.01)

(56) References Cited

U.S. PATENT DOCUMENTS

| | | | |
|---|---|---|---|
| 6,942,623 | B2 | 9/2005 | Robergs et al. |
| 2005/0217671 | A1 | 10/2005 | Adams |
| 2020/0121222 | A1* | 4/2020 | Becker .................. A61B 5/093 |
| 2020/0359935 | A1* | 11/2020 | Clemensen ......... A61M 16/085 |

FOREIGN PATENT DOCUMENTS

| | | | |
|---|---|---|---|
| WO | WO-2017079425 A1 * | 5/2017 | |
| WO | 2019094680 A1 | 5/2019 | |

OTHER PUBLICATIONS

International Search Report for PCT/EP2021/051549 filed Jan. 25, 2021.
Davies, R et al., "Breath-by-breath measurement of oxygen consumption and Fio 2-Feo 2 with increased oxygen demand", ACTA Anaesthesiologic Scandinavica, vol. 35, No. 3, (Apr. 1, 1991), pp. 201-204.
Mautz, W.J. "Calibration of Respiratory Gas Exchange Measurements in Inhalation Toxicology Studies". Fundamental and Applied Toxicology 18, 144-148 (1992).

\* cited by examiner

|  |  | err FiO2 | -2.50% | -2.00% | -1.50% | -1.00% | -0.50% | -0.25% | 0.00% | 0.25% | 0.50% | 1.00% | 1.50% | 2.00% | 2.50% |
|---|---|---|---|---|---|---|---|---|---|---|---|---|---|---|---|
| FiO2=0.4 | Com. Ex. | err VO2 % | -69 | -55 | -42 | -28 | -14 | -7 | 0 | 7 | 14 | 29 | 44 | 59 | 75 |
|  | Fig. 3 | err VO2 % | -2 | -1 | -1 | -1 | 0 | 0 | 0 | 0 | 0 | 1 | 1 | 1 | 2 |
|  | *Fig. 3 | err VO2 % | -1 | -1 | -1 | 0 | 0 | 0 | 0 | 0 | 0 | 0 | 1 | 1 | 1 |
|  | Fig. 4 | err VO2 % | 0 | 0 | 0 | 0 | 0 | 0 | 0 | 0 | 0 | 0 | 0 | 0 | 0 |
| FiO2=0.6 | Com. Ex. | err VO2 % | -101 | -82 | -62 | -42 | -21 | -11 | 0 | 11 | 22 | 44 | 67 | 90 | 114 |
|  | Fig. 3 | err VO2 % | -3 | -2 | -2 | -1 | -1 | 0 | 0 | 0 | 1 | 1 | 2 | 2 | 3 |
|  | *Fig. 3 | err VO2 % | -1 | -1 | -1 | 0 | 0 | 0 | 0 | 0 | 0 | 0 | 1 | 1 | 1 |
|  | Fig. 4 | err VO2 % | 0 | 0 | 0 | 0 | 0 | 0 | 0 | 0 | 0 | 0 | 0 | 0 | 0 |
| FiO2=0.8 | Com. Ex. | err VO2 % | -190 | -156 | -120 | -82 | -42 | -21 | 0 | 22 | 44 | 90 | 139 | 190 | 245 |
|  | Fig. 3 | err VO2 % | -5 | -4 | -3 | -2 | -1 | -1 | 0 | 1 | 1 | 2 | 3 | 5 | 6 |
|  | *Fig. 3 | err VO2 % | -1 | -1 | -1 | 0 | 0 | 0 | 0 | 0 | 0 | 0 | 1 | 1 | 1 |
|  | Fig. 4 | err VO2 % | 0 | 0 | 0 | 0 | 0 | 0 | 0 | 0 | 0 | 0 | 0 | 0 | 0 |

Figure 5

OXYGEN CONSUMPTION DETERMINATION

CROSS-REFERENCE TO RELATED APPLICATIONS

This patent application claims the priority benefit under 35 U.S.C. § 119(e) of U.S. Provisional Application No. 62/968,197, filed on Jan. 31, 2020, the contents of which are herein incorporated by reference.

TECHNICAL FIELD OF THE INVENTION

The invention relates to a method, apparatus and tangible machine-readable medium for determining a subject's oxygen consumption

BACKGROUND OF THE INVENTION

Measurements of oxygen consumption volume (VO2) and carbon dioxide production volume (VCO2) may be useful in certain applications such as anesthesia, critical care and nutrition management. Simultaneous measurements of VO2 and VCO2 may be referred to as metabolic monitoring since the amount of energy expenditure of the body can be inferred by these two measurements (this is known as 'indirect calorimetry'). VO2 measurements are of particular interest in subjects such as critical patients since VO2 is intimately related to the transport of oxygen from the lungs to the tissues that need this oxygen. As such, VO2 may provide significant insights into the cardiovascular and metabolic status of a subject.

VO2 is defined as the difference between the inhaled volume of O2 ($V_{inh}O2$) and the exhaled volume of O2 ($V_{exh}O2$), as shown by the following formula:

$$VO2 = V_{inh}O2 - V_{exh}O2$$

Both the inhaled and exhaled oxygen volumes are determined (e.g., by direct measurement or indirect estimation) to infer the subject's VO2.

Size, cost and accuracy of existing systems have limited the application of VO2 measurements. Thus, VO2 measurements may not be commonly performed in certain clinical scenarios.

Expensive and bulky metabolic cart systems may be used for measuring the oxygen consumption volume. These systems may require a long start-up time and may be used intermittently.

More compact systems, which may be known as breath-by-breath systems, rely on high-frequency measurements of O2 concentration within a gas flow. O2 sensors for performing such measurements may be regarded as expensive. Their accuracy may be highly dependent on the precise time alignment of the measured O2 concentration and gas flow waveforms.

In certain systems for determining the oxygen concentration in gas exhaled by a subject, $V_{exh}O2$ is measured directly whereas $V_{inh}O2$ is inferred indirectly. Mechanically ventilated patients often inhale a mixture of gas with an oxygen fraction (FiO2) higher than the 21% typical of ambient air. The FiO2 value is used as an input for the calculation of and, in turn, of VO2. The FiO2 value may be estimated from a manually-input value (e.g., from the FiO2 value set by the ventilator).

Once the FiO2 value has been estimated, $V_{inh}O2$ can be calculated by measuring the instantaneous inhalation gas flow rate ($Q_{inh}$) and integrating the product of FiO2 and $Q_{inh}$ over the inhalation time:

$$V_{inh}O2 = \int_{inh} F_i O2(t) \cdot Q_{inh}(t) dt$$

This calculation requires relatively fast measurements of the FiO2 value and precise alignment of the FiO2 and $Q_{inh}$ waveforms (similar to so-called breath-by-breath systems).

Another way to calculate is by assuming that FiO2 is sufficiently constant during the breath to be approximated with its time average (indicated as 'tilde FiO2', $\widetilde{F_iO2}$) and using the Haldane transformation to estimate the inhalation volume from the (measured) exhalation volume $V_{exh}$. The Haldane equation is based on the assumption that the volumes of inhaled and exhaled nitrogen are equal. By measuring the gas flow only during the exhalation phase (from which the volume is computed), this equation allows the computation of the inhalation volume $V_{inh}$ as follows:

$$V_{inh} = V_{exh}((1 - \overline{F_eO2} - \overline{F_eCO2}))/(1 - \widetilde{F_iO2}))$$

Where $\overline{F_eO2}$ refers to the measured fraction (i.e., the concentration) of oxygen of sampled exhalation gas and where $\overline{F_eCO2}$ refers to the measured fraction (i.e., the concentration) of carbon dioxide sampled exhalation gas. $V_{inh}O2$ is then approximated as:

$$V_{inh}O2 = V_{inh} \cdot \widetilde{F_iO2} = V_{exh}((1 - \overline{F_eO2} - \overline{F_eCO2}))/(1 - \widetilde{F_iO2})) \cdot \widetilde{F_iO2}$$

At high FiO2 levels (e.g., FiO2>60%), where volumes of nitrogen are very small, the Haldane equation becomes ill-conditioned and severely affects the accuracy of the VO2 computation. For this reason, certain commercial metabolic measurement systems are not indicated for use with FiO2>60%. Even at more moderate FiO2 levels (e.g., FiO2 of order 40%), the VO2 computation may still be erroneous.

With lower levels of FiO2, the Haldane transformation is more accurate, but the accuracy of the resulting $V_{inh}O2$ estimate heavily depends on the accuracy of the FiO2 estimation, as well as on the capability of the ventilator to maintain FiO2 as constant throughout the inhalation phase.

SUMMARY OF THE INVENTION

Aspects or embodiments described herein relate to improving oxygen consumption monitoring. Aspects or embodiments described herein may obviate one or more problems associated with oxygen consumption monitoring in certain scenarios.

According to a first aspect, a method is described. The method may be a computer-implemented method. The method comprises receiving an indication of an oxygen fraction in a sample of inhalation gas delivered by a ventilator for inhalation by a subject. The method further comprises receiving an indication of an oxygen fraction in a sample of exhalation gas exhaled by the subject. The method comprises receiving an indication of a measurement of a flow rate of the exhalation gas. The method comprises determining the subject's oxygen consumption based on the indication.

In some embodiments, the indication of the oxygen fraction in the sample of the inhalation gas and the oxygen fraction in the sample of the exhalation gas comprises an indication of a difference in the oxygen fraction between the samples of the inhalation gas and the exhalation gas.

In some embodiments, the indication of the difference is determined by an oxygen concentration sensor exposed to both the sample of the inhalation gas and the sample of the exhalation gas. The samples of the inhalation gas and the exhalation gas may be isolated from each other.

In some embodiments, the indication further comprises a carbon dioxide fraction in the sample of the exhalation gas exhaled by the subject. The subject's oxygen consumption, VO2, may be determined according to:

$$VO2=V_{exh}*\overline{FiO2-FeO2}+V_{exh}*(\overline{FiO2-FeO2}-\overline{FeCO2})*((\widetilde{FiO2})/(1-\widetilde{FiO2})),$$

where $V_{exh}$ refers to a volume of the exhaled gas determined based on the measurement of the flow rate of the exhalation gas, $\overline{FiO2-FeO2}$ refers to the difference in the oxygen fraction, $\overline{FeCO2}$ refers to the carbon dioxide fraction in the sample of the exhalation gas, and $\widetilde{FiO2}$ refers to a time-averaged oxygen fraction in the sample of the inhalation gas.

In some embodiments, the indication further comprises a measurement of a flow rate of the inhalation gas.

In some embodiments, the subject's oxygen consumption, VO2, is determined according to:

$$VO2=V_{exh}*\overline{FiO2-FeO2}+(V_{inh}-V_{exh})*\widetilde{FiO2},$$

where $V_{exh}$ refers to a volume of the exhaled gas determined based on the measurement of the flow rate of the exhalation gas, $\overline{FiO2-FeO2}$ refers to the difference in the oxygen fraction, $V_{inh}$ refers to a volume of the inhaled gas determined based on the measurement of the flow rate of the inhalation gas, and $\widetilde{FiO2}$ refers to a time-averaged oxygen fraction in the sample of the inhalation gas.

In some embodiments, the indication further comprises a measurement of a flow rate of the inhalation gas. The subject's oxygen consumption, VO2, may be determined according to:

$$VO2=\overline{FiO2}*V_{inh}-\overline{FeO2}*V_{exh},$$

where $\overline{FiO2}$ refers to a measurement of an oxygen fraction in the sample of the inhalation gas, $V_{inh}$ refers to a volume of the inhaled gas determined based on the measurement of the flow rate of the inhalation gas, $\overline{FeO2}$ refers to a measurement of an oxygen fraction in the sample of the exhalation gas, and $V_{exh}$ refers to a volume of the exhaled gas determined based on the measurement of the flow rate of the exhalation gas.

According to a second aspect, a tangible machine-readable medium is described. The tangible machine-readable medium stores instructions, which when executed by at least one processor, cause the at least one processor to implement any method described herein such as according to the first aspect or any embodiments described herein.

According to a third aspect, apparatus is described. The apparatus comprises a first chamber for sampling inhalation gas delivered by a ventilator for inhalation by a subject. The apparatus further comprises a second chamber for sampling exhalation gas exhaled by the subject. The apparatus further comprises a gas concentration sensing system. The gas concentration sensing system is configured to obtain an indication of an oxygen fraction of sampled inhalation gas in the first chamber and an oxygen fraction of sampled exhalation gas in the second chamber. The gas concentration sensing system is further configured to send the indication to a determining module for determining the subject's oxygen consumption based on the indication and a measurement of a flow rate of the exhalation gas.

In some embodiments, the first chamber is configured to allow sampled inhalation gas to be mixed with previously-sampled inhalation gas in the first chamber. The second chamber may be configured to allow sampled exhalation gas to be mixed with previously-sampled exhalation gas in the second chamber.

In some embodiments, the apparatus further comprises the determining module.

In some embodiments, the gas concentration sensing system comprises an oxygen concentration sensor. The oxygen concentration sensor may comprise a first oxygen sensing portion configured to be exposed to the inhalation gas. The oxygen concentration sensor may further comprise a second oxygen sensing portion configured to be exposed to the exhalation gas. The gas concentration sensing system may be able to determine a difference between the oxygen fraction in the sampled inhalation gas and the oxygen fraction in the sampled exhalation gas.

In some embodiments, the gas concentration sensing system comprises a first oxygen concentration sensor configured to be exposed to the inhalation gas. The gas concentration sensing system may further comprise a second oxygen concentration sensor configured to be exposed to the exhalation gas. The gas concentration sensing system may be able to determine the oxygen fraction in the sampled inhalation gas and the sampled exhalation gas.

In some embodiments, the apparatus comprises a carbon dioxide concentration sensor. The carbon dioxide concentration sensor may be configured to determine a carbon dioxide fraction in the sampled exhalation gas.

In some embodiments, the apparatus comprises an exhalation gas flow sensor for measuring the flow rate of the exhalation gas. In some embodiments, the apparatus comprises an inhalation gas flow sensor for measuring the flow rate of the inhalation gas.

Certain technical benefits may be realized by these aspects or embodiments. For example, these aspects or embodiments may at least one of: improve the accuracy of O2 measurements of inhalation gas; facilitate fast and/or high frequency O2 measurements; reduce cost associated with a system for determining oxygen consumption while meeting certain criteria in terms of accuracy of oxygen consumption determination; reduce a need for time alignment of oxygen concentration measurements and gas flow rate waveforms; provide a compact system for measuring VO2 consumption; and improve accuracy of measurements of oxygen consumption at certain levels of FiO2 which may otherwise cause errors in the measurements.

These and other aspects of the invention will be apparent from and elucidated with reference to the embodiment(s) described hereinafter.

BRIEF DESCRIPTION OF DRAWINGS

Exemplary embodiments of the invention will now be described, by way of example only, with reference to the following drawings, in which:

FIG. 5 is a table comparing performance of certain apparatus described herein.

DETAILED DESCRIPTION OF THE EMBODIMENTS

Figure 1:
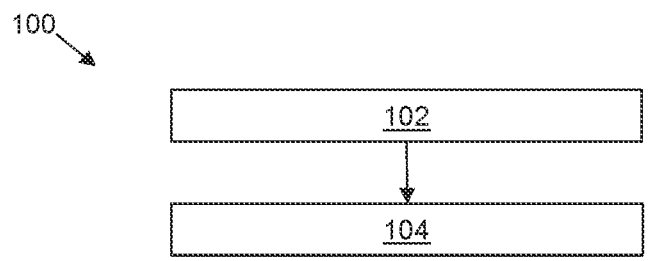
FIG. 1 refers to a method of determining a subject's oxygen consumption according to an embodiment.

FIG. 1 shows a method 100, which may be a computer-implemented method, of determining a subject's oxygen consumption. The method 100 comprises receiving, at block 102, an indication of certain measurements performed by certain apparatus, as will be described in more detail herein.

In this embodiment, the indication comprises an oxygen fraction (FiO2) in a sample of inhalation gas delivered by a ventilator for inhalation by a subject. The oxygen fraction may refer to an oxygen concentration of the inhalation gas such as measured in a mixing chamber for sampling the inhalation gas.

The indication further comprises an oxygen fraction in a sample of exhalation gas exhaled by the subject. The oxygen fraction may refer to an oxygen concentration of the exhalation gas such as measured in a mixing chamber for sampling the exhalation gas.

The indication further comprises a measurement of a flow rate ($Q_{exh}$) of the exhalation gas. The flow rate of the exhalation gas may refer to a rate of volume (e.g., volume per unit time) of gas generated due to the subject exhaling. The flow rate may be determined using a gas flow sensor configured to measure the flow rate of the exhalation gas.

The method 100 further comprises, at block 104, determining the subject's oxygen consumption based on the indication. The indication may provide sufficient information in order to allow for improved oxygen consumption monitoring and/or obviating one or more problems associated with oxygen consumption monitoring in certain scenarios.

Obtaining the indication of the oxygen fraction (FiO2) in the sample of the inhalation gas delivered by a ventilator for inhalation by a subject may improve the accuracy of O2 measurements of inhalation gas. A more accurate measurement of the FiO2 value may reduce the error in the calculation of the oxygen consumption.

In some embodiments, the indication of the oxygen fraction in the sample of the inhalation gas and the oxygen fraction in the sample of the exhalation gas comprises an indication of a difference in the oxygen fraction between the samples of the inhalation gas and the exhalation gas.

The indication of the difference may be determined by an oxygen concentration sensor, as will be described in greater detail herein, exposed to both the sample of the inhalation gas and the samples of the exhalation gas. In this case, the samples of the inhalation gas and the exhalation gas are isolated from each other. In other similar words, the sample of the inhalation gas and the sample of the exhalation gas may be isolated from each other such that no mixing of the samples of the inhalation gas and exhalation gas may occur. However, the oxygen concentration sensor may be configured to measure (e.g., simultaneously measure) the oxygen concentration level (e.g., oxygen fraction) in each of the samples of the inhalation gas and the exhalation gas by virtue of a first sensing portion of the oxygen concentration sensor being exposed to the sample of the inhalation gas and a second, separate, sensing portion of the oxygen concentration sensor being exposed to the sample of the exhalation gas. For example, the oxygen concentration sensor may be configured to measure a differential in the oxygen concentration level (i.e., between the samples of the inhalation gas and the exhalation gas).

In some embodiments, the indication further comprises a carbon dioxide fraction (e.g., carbon dioxide concentration) in the sample of the exhalation gas exhaled by the subject. Where the carbon dioxide fraction is measured (e.g., using a carbon dioxide concentration sensor), the subject's oxygen consumption, VO2, may be determined according to:

$$VO2 = V_{exh} * \overline{FiO2 - FeO2} + V_{exh} * (\overline{FiO2 - FeO2 - FeCO2}) * ((\widetilde{FiO2})/(1 - \widetilde{FiO2})),$$

where $V_{exh}$ refers to a volume of the exhaled gas determined based on the measurement of the flow rate of the exhalation gas ($Q_{exh}$), $\overline{FiO2 - FeO2}$ refers to the difference in the oxygen fraction, $\overline{FeCO2}$ refers to the carbon dioxide fraction in the sample of the exhalation gas, and $\widetilde{FiO2}$ refers to a time-averaged oxygen fraction in the sample of the inhalation gas.

In some embodiments, the indication further comprises a measurement of a flow rate of the inhalation gas ($Q_{inh}$). The flow rate may be determined using a flow sensor configured to measure the flow rate of the inhalation gas.

Where the measurement of the flow rate of the inhalation gas is determined, the subject's oxygen consumption, VO2, may be determined according to:

$$VO2 = V_{exh} * \overline{FiO2 - FeO2} + (V_{inh} - V_{exh}) * \widetilde{FiO2},$$

where $V_{exh}$ refers to a volume of the exhaled gas determined based on the measurement of the flow rate of the exhalation gas, $\overline{FiO2 - FeO2}$ refers to the difference in the oxygen fraction, $V_{inh}$ refers to a volume of the inhaled gas determined based on the measurement of the flow rate of the inhalation gas, and $\widetilde{FiO2}$ refers to a time-averaged oxygen fraction in the sample of the inhalation gas.

In some embodiments, the indication further comprises a measurement of a flow rate of the inhalation gas where the subject's oxygen consumption, VO2, is determined according to:

$$VO2 = \overline{FiO2} * V_{inh} - \overline{FeO2} * V_{exh},$$

where $\overline{FiO2}$ refers to a measurement of an oxygen fraction in the sample of the inhalation gas, $V_{inh}$ refers to a volume of the inhaled gas determined based on the measurement of the flow rate of the inhalation gas, $\overline{FeO2}$ refers to a measurement of an oxygen fraction in the sample of the exhalation gas, and $V_{exh}$ refers to a volume of the exhaled gas determined based on the measurement of the flow rate of the exhalation gas.

Figure 2:
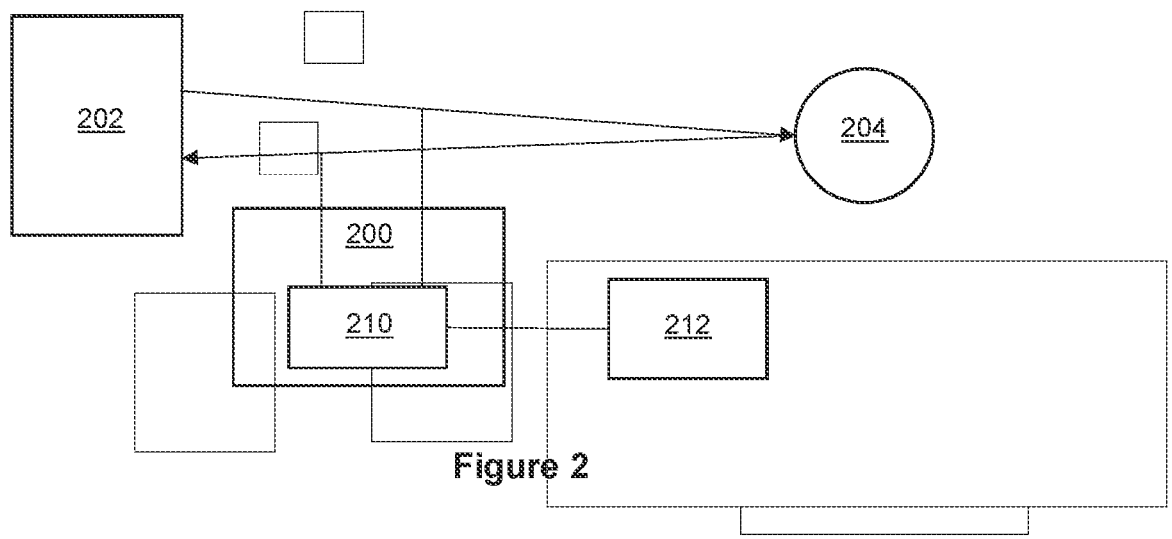
FIG. 2 is a schematic drawing of apparatus according to an embodiment.

FIG. 2 shows an apparatus 200, which may facilitate or at least partially implement certain methods described herein such as described in relation to the method 100. The apparatus 200 comprises a gas concentration sensing system 210.

The gas concentration sensing system 210 is configured to obtain an indication of an oxygen fraction in a sample of inhalation gas delivered by a ventilator 202 for inhalation by a subject 204. The arrow extending from the ventilator 202 to the subject 204 represents the inhalation gas delivered by the ventilator 202 to the subject 204.

The gas concentration sensing system 210 is further configured to obtain an indication of an oxygen fraction in a sample of exhalation gas exhaled by the subject 204. The arrow extending from the subject 204 to the ventilator 202 represents the exhalation gas from the subject 204 which may, in some cases, by received by the ventilator 202 or otherwise disposed of.

Accordingly, the gas concentration sensing system 210 may provide at least part of the indication as referred to in block 102 of the method 100 (i.e., the indication provided by the gas concentration sensing system 210 may comprise an oxygen fraction in the sample of the inhalation gas and an oxygen fraction in the sample of the exhalation gas).

The gas concentration sensing system 210 is further configured to send the indication to a determining module 212 for determining the subject's oxygen consumption based on the indication and a measurement of a flow rate of the exhalation gas. The determining module 212 may comprise processing circuitry for determining the subject's oxygen consumption. The determining module 212 may implement block 104 of the method 100, for example, by receiving an indication of a measurement of a flow rate ($Q_{exh}$) of the exhalation gas, as will be discussed in more detail herein.

In some embodiments, the determining module 212 may form part of the apparatus 200 itself (e.g., the apparatus 200 may comprise processing circuitry for determining the subject's oxygen consumption). In some embodiments, the determining module 212 may be implemented by a separate computing device such as a personal computing device, server or cloud-based service.

Figure 3:
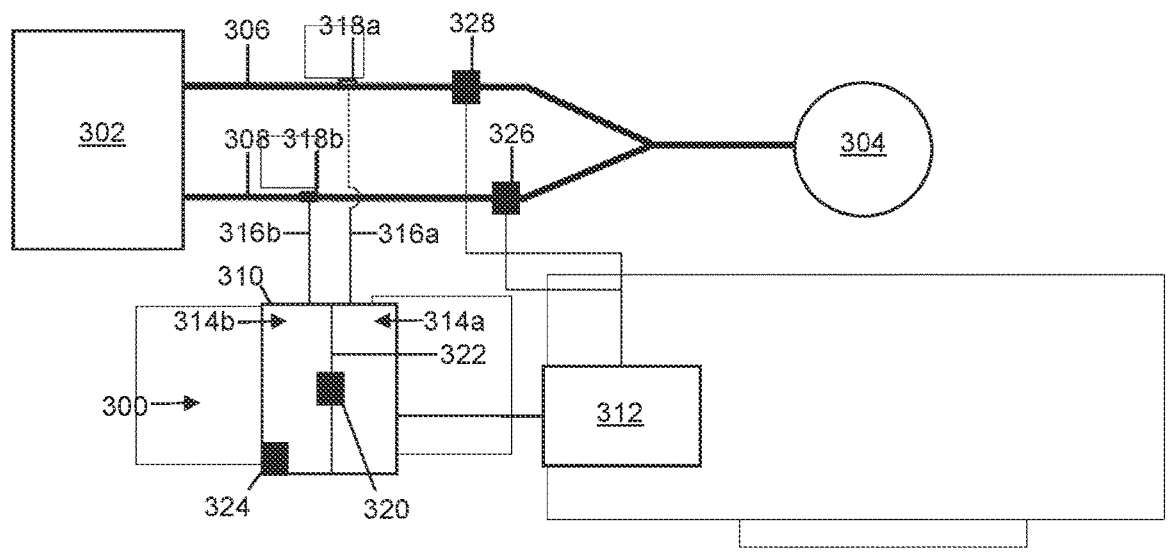
FIG. 3 is a schematic drawing of apparatus according to an embodiment.

FIG. 3 shows an apparatus 300, which may facilitate or at least partially implement certain methods described herein such as the method 100. Similar to the apparatus 200, the apparatus 300 comprises a gas concentration sensing system 310, which may provide the same or similar functionality to the apparatus 200. Features of the apparatus 300 corresponding to the apparatus 200 are represented by reference signs incremented by 100 compared with those indicated in FIG. 2.

The gas concentration sensing system 310 is configured to obtain an indication of an oxygen fraction in a sample of inhalation gas delivered by a ventilator 302 for inhalation by a subject 304. The inhalation gas is delivered from the ventilator 302 to the subject 304 via an inhalation gas connector 306 (e.g., a pipe) and an interface (not shown) such as a facial mask or nasal cannula for allowing the subject to inhale the inhalation gas.

The gas concentration sensing system 310 is further configured to obtain an indication of an oxygen fraction in a sample of exhalation gas exhaled by the subject 304. The exhalation gas is delivered from the subject 304 to the ventilator 302 via the interface and an exhalation gas connector 308 (e.g., a pipe).

Similar to FIG. 2, the gas concentration sensing system 310 of FIG. 3 is further configured to send the indication to a determining module 312 for determining the subject's oxygen consumption based on the indication and a measurement of a flow rate of the exhalation gas.

The gas concentration sensing system 310 comprises a first chamber 314a for sampling the inhalation gas and a second chamber 314b for sampling the exhalation gas. The first chamber 314a is configured to allow sampled inhalation gas to be mixed with previously-sampled inhalation gas in the first chamber 314a. The second chamber 314b is configured to allow sampled exhalation gas to be mixed with previously-sampled exhalation gas in the second chamber 314b.

A first sampling line 316a connects the inhalation gas connector 306 to the first chamber 314a. A second sampling line 316b connects the exhalation gas connector 308 to the second chamber 314b. Although not shown by FIG. 3, each of the sampling lines 316a, 316b may comprise two sampling connectors (e.g., two separate pipes). A first of these sampling connectors is used for collecting gas to be sampled from the respective gas connector 306, 308 (i.e., to allow the gas to be sampled to flow from the respective gas connector 306, 308 to the respective chamber 314a, 314b). A second of these sampling connectors is used for returning sampled gas from the chambers 314, 314b (i.e., to allow the sampled gas to flow from the respective chamber 314a, 314b to the respective gas connector 306, 308). Thus, the sampling lines 316a, 316b allow sampled gas to flow from the respective gas connectors 306, 308 to the respective chambers 314a, 314b and then be returned to the respective gas connectors 306, 308.

The sampling lines 316a, 316b may divert a fixed percentage of the instantaneous gas flow passing through the respective gas connector 306, 308 to the corresponding chamber 314a, 314b. This may be referred to as proportional sampling. This proportional sampling may ensure that the gases in the chambers 314a, 314b contain the respiratory gases (e.g., oxygen, nitrogen, and carbon dioxide) in the same proportion as the overall inhalation gas and exhalation gas. In some embodiments, the proportional sampling can be achieved via a passive system where the sampled gas flows naturally through the sampling lines 316a, 316b. In some embodiments, an active component such as a gas pump and/or active valve may be used to sample flow in a proportional fashion. In some embodiments, the sampling of the inhalation and exhalation gases may be performed at a constant gas flow rate (e.g., the sampling may ensure that the gas flows through the sampling lines 316a, 316b at a constant rate rather than corresponding to the instantaneous gas flow through the respective gas connector 306, 308).

A first sampling port 318a is provided for connecting the two sampling connectors of the first sampling line 316a to the inhalation gas connector 306. A second sampling port 318b is provided for connecting the two sampling connectors of the second sampling line 316b to the exhalation gas connector 308. Although not shown by FIG. 3, the sampling ports 318a, 318b may each comprise an inlet and an outlet provided in a wall of the respective gas connectors 306, 308. Each respective inlet may be connected to its respective chamber 314a, 314b via the first of the sampling connectors of each of the sampling lines 316a, 316b. Each respective outlet may be connected to its respective chamber 314a, 314b via the second of the sampling connectors of each of the sampling lines 316a, 316b.

The gas concentration sensing system 310 comprises an oxygen concentration sensor 320. The oxygen concentration sensor 320 comprises a first oxygen sensing portion configured to be exposed to the inhalation gas (e.g., in the first chamber 314a). The oxygen concentration sensor 320 further comprises a second oxygen sensing portion configured to be exposed to the exhalation gas (e.g., in the second chamber 314b). The oxygen concentrator sensor 320 may enable the gas concentration sensing system 310 to determine a difference between the oxygen fraction in the sample of the inhalation gas and the oxygen fraction in the sample of the exhalation gas.

The first and second chambers 314a, 314b are isolated from each other by an isolating wall 322 such that there is no mixing of the gas between the two chambers 314a, 314b. The oxygen concentration sensor 320 is disposed in an aperture in the isolating wall 322 between the first and second chambers 314a, 314b in such a way that first oxygen sensing portion is exposed to the sample of the inhalation gas in the first chamber 314a and the second oxygen sensing portion is exposed to the sample of the exhalation gas in the second chamber 314b. Thus, the first and second oxygen sensing portions of the oxygen concentration sensor 320 are exposed to the oxygen concentration in each of the first and second chambers 314a, 314b and the sensor 320 determines the difference in the oxygen concentration between the samples in the first and second chambers 314a, 314b. Thus, in some embodiments, the oxygen concentration sensor 320 may function as a differential oxygen concentration sensor.

In some embodiments, the chambers 314a, 314b may be referred to as mixing chambers (e.g., for allowing the sampled gas to be mixed over a period of time). The chambers 314a, 314b may avoid the need for a fast or high frequency oxygen concentration sensor to be used since the change in concentration of the gas in the chambers 314a, 314b may be a relatively slow process. Further, where the measurements are performed in mixing chambers, issues with complex time alignment of oxygen concentration measurements and gas flow rate waveforms may be avoided. Thus, a relatively slow oxygen concentration sensor may be used for measuring the oxygen concentration. The use of a single (and potentially relatively slow) oxygen concentration sensor 320 in this embodiment may save costs associated with the apparatus 300 compared with using a faster and/or more oxygen concentration sensors.

The two chambers 314a, 314b may be relatively small chambers, which may provide a relatively compact apparatus 300. In some embodiments the two chambers 314a, 314b may share the same external wall and isolating wall 322 for isolating the two chambers 314a, 314b. The chambers 314a, 314b may collect small representative samples of both the inhaled and exhaled gases, which, being mixed inside said chambers, can be analyzed by a relatively slow, inexpensive oxygen concentration sensor, as described above. The use of two isolated chambers 314a, 314b may allow for the measurements of the oxygen volume supplied by the ventilator 302 (via the inhalation gas connector 306) and returned to the ventilator 302 (via the exhalation gas connector 308), which by definition (in the absence of leaks) is equal to the volume of oxygen consumed by the patient (VO2). The resulting VO2 (and potentially also VCO2) measurements are provided in ml per breath or in ml/min as average over a given amount of time (e.g., one or more minutes). Sampling only part of the inhalation and exhalation gases may allow the apparatus 300 to be provided in relatively compact form.

In some embodiments, a determination of the carbon dioxide fraction may be used in the computation of the oxygen consumption and/or carbon dioxide production. Thus, in some embodiments, the apparatus 300 further comprises a carbon dioxide concentration sensor 324 configured to determine a carbon dioxide fraction in the sample of the exhalation gas.

An exhalation gas flow sensor 326 is provided for measuring the flow rate of the exhalation gas (which may be used by the determining module 312 to calculate the oxygen consumption). In some embodiments, the apparatus 300 comprises the exhalation gas flow sensor 326. In some embodiments, the exhalation gas flow sensor 326 is provided as part of or used in conjunction with the ventilator 302 (i.e., separate from the apparatus 300).

In some embodiments, an inhalation gas flow sensor 328 is provided for measuring the flow rate of the inhalation gas (which may be used by the determining module 312 to calculate the oxygen consumption). In some embodiments, the apparatus 300 comprises the inhalation gas flow sensor 328. In some embodiments, the inhalation gas flow sensor 328 is provided as part of or used in conjunction with the ventilator 302 (i.e., separate from the apparatus 300).

As will be discussed in more detail below, the determination of the oxygen fraction, carbon dioxide fraction and the flow rate of the exhalation gas may be used to determine the oxygen consumption (and where appropriate, certain other parameters of interest such as carbon dioxide production, energy expenditure and/or respiratory quotient).

An example nominal (ground-truth) VO2 for a mechanically ventilated subject may be 350 ml/min. For example, the subject may consume an average of 350 ml/min of oxygen and produce 200 ml/min of carbon dioxide. The subject may be ventilated with a minute ventilation of 5.85 lpm, i.e., the total expired gases amount to an average of 5.85 liters per minute, and with a fraction of inspired oxygen (FiO2) of 40%, 60% and 80% (i.e., 3 different example scenarios).

The general equation to estimate VO2 is:

$$VO2 = \overline{FiO2} * V_{inh} - \overline{FeO2} * V_{exh}$$

where the bar indicates concentrations of the (sampled) mixed gases (i.e., the inspiratory gases are represented by $\overline{FiO2}$; and the expiratory gases are represented by $\overline{FeO2}$).

The different configurations of certain embodiments described herein lead to different implementations of the above general equation for VO2.

In some examples, neither $\overline{FiO2}$ nor $V_{inh}$ are measured. The latter may be estimated via the Haldane transformation and the former may either be measured as a time-averaged value (which may be different from the mixed gas average concentration) via a dedicated oxygen concentration sensor or estimated from the ventilator 302 setting (which may be affected by errors). To indicate that the values of FiO2 are not from measurements of mixed gases and therefore are affected by errors, the tilde symbol is used in lieu of the bar. The oxygen consumption may thus be expressed as:

$$VO2 = \widetilde{FiO2} * V_{exh} * ((1 - \overline{F_eO2} - \overline{F_eCO2})/(1 - \widetilde{F_iO2})) - \overline{FeO2} * V_{exh},$$

where $\overline{F_eCO2}$ refers to the concentration of the carbon dioxide in the sampled (e.g., mixed) exhalation gas. Accordingly, this expression for the oxygen consumption may be affected by errors, particularly where $\widetilde{F_iO2}$ is large (e.g., much greater than 20% such as >40% or >60%).

For the apparatus 300 of FIG. 3, the formula used to compute VO2 can be modified in the light of the fact that neither FiO2 nor FeO2 are measured in the chambers 314a, 314b. Rather, the difference in oxygen concentration ($\overline{FiO2} - \overline{FeO2}$) is measured by the oxygen concentration sensor 320. $V_{inh}$ is again computed via the Haldane equation. After algebraic manipulation, the following formula for oxygen consumption using the apparatus of FIG. 3 is obtained:

$$VO2 = V_{exh} * \overline{FiO2 - FeO2} + V_{exh} * (\overline{FiO2 - FeO2} - \overline{FeCO2}) * ((\widetilde{FiO2})/(1 - \widetilde{FiO2})),$$

Note that $\widetilde{FiO2}$ is used by itself in the second term of the formula and, since it is not measured but estimated (e.g., from the ventilator 302 setting), the value may be affected by error.

In some embodiments, the inhalation gas flow sensor 328 may be used to provide an indication of a measurement of $V_{inh}$. With the same configuration but adding a flow sensor on the inhalation side, the Haldane equation is not used and the formula for oxygen consumption can be expressed as:

$$VO2 = V_{exh} * \overline{FiO2 - FeO2} + (V_{inh} - V_{exh}) * \widetilde{FiO2}$$

Thus, in certain embodiments where the inhalation gas flow sensor 328 is provided, it may not be necessary to use a carbon dioxide concentration sensor in order to calculate the oxygen consumption, which may save on costs and/or complexity of the apparatus 300.

Figure 4:
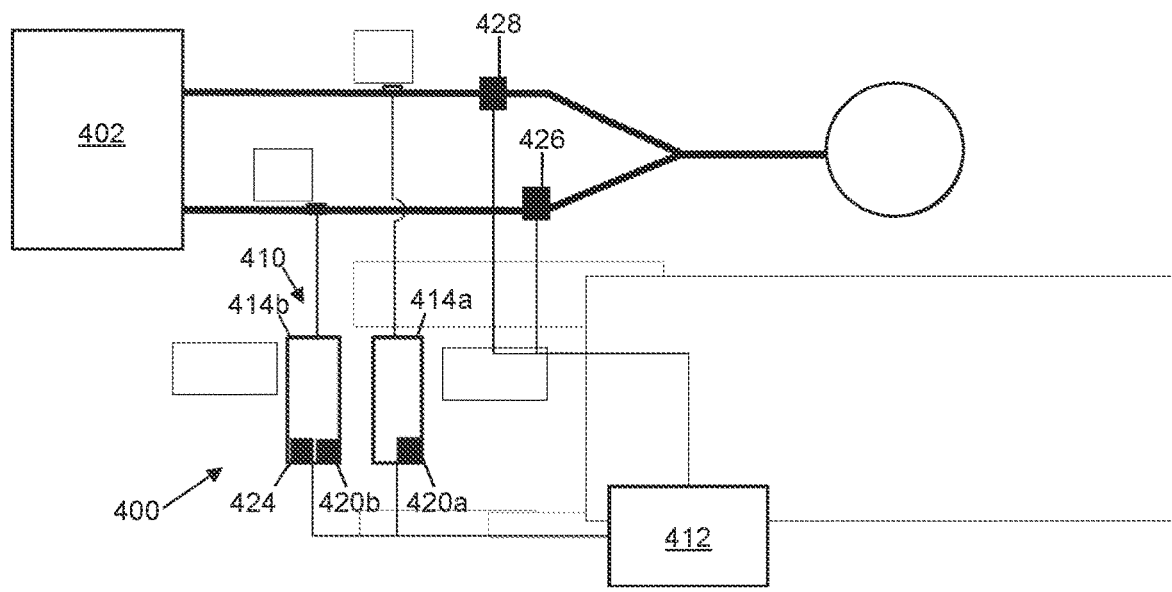
FIG. 4 is a schematic drawing of apparatus according to an embodiment.

FIG. 4 shows an apparatus 400, which may facilitate or at least partially implement certain methods described herein such as the method 100. Similar to the apparatus 200, 300, the apparatus 400 comprises a gas concentration sensing system 410, which may provide the same or similar functionality to the apparatus 200, 300. Features of the apparatus 400 corresponding to the apparatus 400 are represented by reference signs incremented by 100 compared with those indicated in FIG. 3. For brevity, certain features of the apparatus 400 are not described where the functionality of the corresponding feature in FIG. 3 is similar or has already been described.

The gas concentration sensing system 410 comprises a first chamber 414a for sampling the inhalation gas and a second chamber 414b for sampling the exhalation gas. Although the first and second chambers 414a, 414b are depicted as being separate from each other, in some embodiments, they may have the same structure as depicted by FIG. 3 albeit with certain differences as noted below.

In contrast to the gas concentration sensing system 310 of FIG. 3, the gas concentration sensing system 410 of FIG. 4 comprises two independent oxygen concentration sensors where a first oxygen concentration sensor 420a is configured to be exposed to the sample of the inhalation gas and a second oxygen concentration sensor 420b is configured to be exposed to the sample of the exhalation gas. The first and second oxygen concentration sensors 420a, 420b enable the gas concentration sensing system 410 to directly determine the oxygen fraction in the sampled inhalation gas and the sampled exhalation gas rather than the difference between the oxygen fraction in the sample of the inhalation gas and the sample of the exhalation gas (as is the case for FIG. 3).

In some embodiments, a determination of the carbon dioxide fraction may be used in the computation of the oxygen consumption and/or carbon dioxide production. Thus, in some embodiments, the apparatus 400 further comprises a carbon dioxide concentration sensor 424 configured to determine a carbon dioxide fraction in the sample of the exhalation gas.

An exhalation gas flow sensor 426 is provided for measuring the flow rate of the exhalation gas. In some embodiments, the apparatus 400 comprises the exhalation gas flow sensor 426. In some embodiments, the exhalation gas flow sensor 426 is provided as part of or used in conjunction with the ventilator 402 (i.e., separate from the apparatus 400).

An inhalation gas flow sensor 428 is also provided for measuring the flow rate of the inhalation gas. In some embodiments, the apparatus 400 comprises the inhalation gas flow sensor 428. In some embodiments, the inhalation gas flow sensor 428 is provided as part of or used in conjunction with the ventilator 402 (i.e., separate from the apparatus 400).

As will be discussed in more detail below, the determination of the oxygen fraction in the first and second chambers 414a, 414b and the flow rate of the inhalation and exhalation gases may be used to determine the oxygen consumption (and where appropriate for certain embodiments, certain other parameters of interest such as carbon dioxide production, energy expenditure and/or respiratory quotient).

Thus, in FIG. 4, the inhalation and exhalation gases are completely and independently characterized (in terms of both volumes and oxygen concentrations). Accordingly, all of the measurements are available and VO2 can be computed with the general formula:

$$VO2 = \overline{FiO2} * V_{inh} - \overline{FeO2} * V_{exh}$$

As will be discussed in more detail below, the apparatus 400 of FIG. 4 may provide measurements leading to a more accurate calculation of the oxygen consumption compared with the measurements provided by, for example, the apparatus 300 of FIG. 3.

FIG. 5 is a table showing the percentage error (err VO2%) in the oxygen consumption calculation for different errors in the oxygen fraction in the sampled inhaled gas for various apparatus configurations. The error in the estimates of VO2 is due to an error in the FiO2 value used in lieu of tilde FiO2 in the equations above. In other words, we introduce the following expression into the equations described above.

$$\widetilde{FiO2} = \overline{FiO2} + errFiO2$$

where the values of errFiO2 are indicated in the table of FIG. 5. The results for four different apparatus configurations are discussed at different levels of FiO2 (i.e., 20%, 40% and 60%). The apparatus configuration 'Com. Ex.' refers to the results for a comparative example where the values of FiO2 are not from measurements of sampled/mixed gases, such as described above. The apparatus configuration 'FIG. 3' refers to the results for the apparatus 300 of FIG. 3 without the measurement provided by the inhalation gas flow sensor 328. The apparatus configuration '*FIG. 3' refers to the results for the apparatus 300 of FIG. 3 but with the measurement provided by the inhalation gas flow sensor 328. The apparatus configuration 'FIG. 4' refers to the results for the apparatus 400 of FIG. 4.

Where there is an error in estimating FiO2, the percentage error in the oxygen consumption results for the comparative example are large, especially so for high values of FiO2. Errors in the assessment of mixed-gas FiO2 of 0.5% produce double-digit relative errors in the final VO2 reading, even at relatively low (e.g., FiO2=40%).

The apparatus 300 of FIG. 3 instead maintains the error within a few percent even when the error in the estimation of FiO2 estimates is above 2%. This error may be considered acceptable for certain applications. As such, with a single (differential) oxygen concentration sensor, the apparatus 300 of FIG. 3 may provide reasonable results in terms of performance while maintaining cost effectiveness. As is apparent from the results in the table, the VO2 error is smaller when an inhalation gas flow sensor is used.

Accordingly, the results for certain embodiments described herein are significantly improved compared with the comparative example. For example, with or without the inhalation gas flow sensor 328, the results for the apparatus 300 of FIG. 3 demonstrate that the VO2 value can be computed with significantly less percentage error than for that of the comparative example. The results for the apparatus 400 of FIG. 4 provide the most improved results compared with the other apparatus configurations. Thus, the measurements taken using the apparatus 400 of FIG. 4 may be used to provide an accurate calculation of the VO2 value. However, the measurements taken using the apparatus 300 of FIG. 3 may still provide a relatively accurate calculation of the VO2 value while also reducing the number of oxygen concentration sensors and/or gas flow sensors used compared with FIG. 4.

Figure 6:
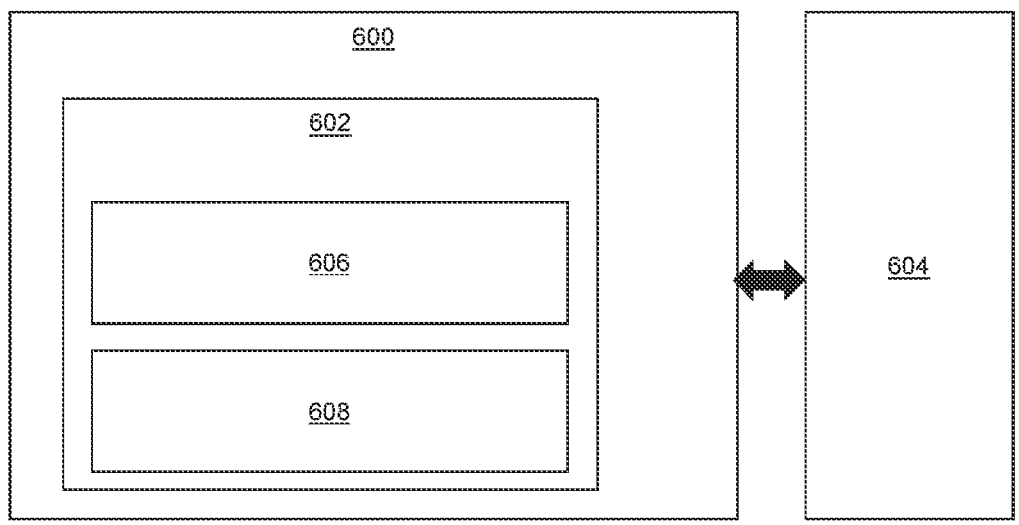
FIG. 6 is a schematic drawing of a machine-readable medium for determining a subject's oxygen consumption according to an embodiment.

FIG. 6 shows a tangible machine-readable medium 600 storing instructions 602 which, when executed by at least one processor 604, cause the at least one processor 604 to implement certain methods described herein (such as the method 100 of FIG. 1). For example, the instructions 602 may comprise instructions 606 to cause the at least one processor 604 to receive an indication of: an oxygen fraction in a sample of inhalation gas delivered by a ventilator for inhalation by a subject; an oxygen fraction in a sample of exhalation gas exhaled by the subject; and a measurement of a flow rate of the exhalation gas. The instructions 602 further comprise instructions 608 to cause the at least one processor 604 to determine the subject's oxygen consumption based on the indication.

One or more features described in one embodiment may be combined with or replace features described in another embodiment. For example, the method 100 of FIG. 1 may be modified based on features described in relation to the apparatus 200, 300, 400 of FIGS. 2, 3 and 4, and vice versa. Further, certain features of one of the apparatus 200, 300, 400 may be combined with, replace or otherwise modify certain features of another of the apparatus 200, 300, 400.

Embodiments in the present disclosure can be provided as methods, apparatus, systems or as a combination of machine readable instructions and processing circuitry. Such machine readable instructions may be included on a non-transitory machine (for example, computer) readable storage medium (including but not limited to disc storage, CD-ROM, optical storage, etc.) having computer readable program codes therein or thereon.

The present disclosure is described with reference to flow charts and block diagrams of the method, devices and systems according to embodiments of the present disclosure. Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine readable instructions may, for example, be executed by a general purpose computer, a special purpose computer, an embedded processor or processors of other programmable data processing devices to realize the functions described in the description and diagrams. In particular, a processor or processing circuitry, or a module thereof, may execute the machine readable instructions. Thus functional modules of the apparatus 200, 300, 400 (for example, the determining module 212, 312, 412) and other devices described herein may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams.

Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practising the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method, comprising:
receiving an indication of:
an oxygen fraction in a sample of inhalation gas delivered by a ventilator for inhalation by a subject;
an oxygen fraction in a sample of exhalation gas exhaled by the subject; and
a measurement of a flow rate of the exhalation gas; and
determining the subject's oxygen consumption based on the indication;
wherein the indication of the oxygen fraction in the sample of the inhalation gas and the oxygen fraction in the sample of the exhalation gas comprises an indication of a difference in the oxygen fraction between the samples of the inhalation gas and the exhalation gas; and
wherein the indication further comprises a carbon dioxide fraction in the sample of the exhalation gas exhaled by the subject, and wherein the subject's oxygen consumption, VO2, is determined according to:

$$VO2 = V_{exh}*\overline{FiO2-FeO2} + V_{exh}*(\overline{FiO2-FeO2-FeCO2})*((\widehat{FiO2}))/(1-\widehat{FiO2})),$$

where $V_{exh}$ refers to a volume of the exhaled gas determined based on the measurement of the flow rate of the exhalation gas, $\overline{FiO2-FeO2}$ refers to the difference in the oxygen fraction, $\overline{FeCO2}$ refers to the carbon dioxide fraction in the sample of the exhalation gas, and $\widehat{FiO2}$ refers to a time-averaged oxygen fraction in the sample of the inhalation gas.

2. The method of claim 1, wherein the indication of the difference is determined by an oxygen concentration sensors exposed to both the sample of the inhalation gas and the sample of the exhalation gas, wherein the samples of the inhalation gas and the exhalation gas are isolated from each other.

3. The method of claim 1, wherein the indication further comprises a measurement of a flow rate of the inhalation gas, and wherein the subject's oxygen consumption, VO2, is determined according to:

$$VO2 = \overline{FiO2}*V_{inh} - \overline{FeO2}*V_{exh},$$

where $\overline{F_iO_2}$ refers to a measurement of an oxygen fraction in the sample of the inhalation gas, $V_{inh}$ refers to a volume of the inhaled gas determined based on the measurement of the flow rate of the inhalation gas, $\overline{F_eO_2}$ refers to a measurement of an oxygen fraction in the sample of the exhalation gas, and $V_{exh}$ refers to a volume of the exhaled gas determined based on the measurement of the flow rate of the exhalation gas.

4. A method, comprising:
receiving an indication of:
   an oxygen fraction in a sample of inhalation gas delivered by a ventilator for inhalation by a subject;
   an oxygen fraction in a sample of exhalation gas exhaled by the subject; and
   a measurement of a flow rate of the exhalation gas; and
determining the subject's oxygen consumption based on the indication;
wherein the indication further comprises a measurement of a flow rate of the inhalation gas; and
wherein the subject's oxygen consumption, VO2, is determined according to:

$$VO2 = V_{exh} * \overline{F_iO_2 - F_eO_2} + (V_{inh} - V_{exh}) * \widetilde{F_iO_2},$$

where $V_{exh}$ refers to a volume of the exhaled gas determined based on the measurement of the flow rate of the exhalation gas, $\overline{F_iO_2 - F_eO_2}$ refers to the difference in the oxygen fraction, $V_{inh}$ refers to a volume of the inhaled gas determined based on the measurement of the flow rate of the inhalation gas, and $\widetilde{F_iO_2}$ refers to a time-averaged oxygen fraction in the sample of the inhalation gas.

5. An apparatus comprising:
a first chamber for sampling inhalation gas delivered by a ventilator for inhalation by a subject;
a second chamber for sampling exhalation gas exhaled by the subject; and
a gas concentration sensing system comprising processor executable code configured to:
   obtain an indication of an oxygen fraction of sampled inhalation gas in the first chamber and an oxygen fraction of sampled exhalation gas in the second chamber; and
   send the indication to a determining module for determining the subject's oxygen consumption based on the indication and a measurement of a flow rate of the exhalation gas;
wherein the gas concentration sensing system comprises an oxygen concentration sensor comprising:
   a first oxygen sensing portion configured to be exposed to the inhalation gas; and
   a second oxygen sensing portion configured to be exposed to the exhalation gas, to enable the gas concentration sensing system to determine a difference between the oxygen fraction in the sampled inhalation gas and the oxygen fraction in the sampled exhalation gas.

6. The apparatus of claim 5, wherein:
the first chamber is configured to allow sampled inhalation gas to be mixed with previously-sampled inhalation gas in the first chamber; and
the second chamber is configured to allow sampled exhalation gas to be mixed with previously-sampled exhalation gas in the second chamber.

7. The apparatus of claim 5, further comprising the determining module.

8. The apparatus of claim 5, further comprising a carbon dioxide concentration sensor configured to determine a carbon dioxide fraction in the sampled exhalation gas.

9. The apparatus of claim 5, further comprising at least one of: an exhalation gas flow sensor for measuring a flow rate of the exhalation gas; and an inhalation gas flow sensor for measuring the flow rate of the inhalation gas.

10. An apparatus comprising:
a first gas mixing chamber for sampling inhalation gas delivered by a ventilator for inhalation by a subject;
a second gas mixing chamber for sampling exhalation gas exhaled by the subject; and
a gas concentration sensing system comprising processor executable code configured to:
   obtain an indication of an oxygen fraction of sampled inhalation gas in the first gas mixing chamber and an oxygen fraction of sampled exhalation gas in the second gas mixing chamber; and
   send the indication to a determining module for determining oxygen consumption of the subject based on the indication and a measurement of a flow rate of the exhalation gas;
wherein the gas concentration sensing system comprises an oxygen concentration sensor comprising:
   a first oxygen sensing portion configured to be exposed to the inhalation gas in the first gas mixing chamber; and
   a second oxygen sensing portion configured to be exposed to the exhalation gas in the second gas mixing chamber, to enable the gas concentration sensing system to determine a difference between the oxygen fraction in the sampled inhalation gas and the oxygen fraction in the sampled exhalation gas.

11. The apparatus of claim 10, wherein the gas concentration sensing system comprises a partition between the first gas mixing chamber and the second gas mixing chamber.

12. The apparatus of claim 11, wherein the oxygen concentration sensor is disposed within the partition.

13. The apparatus of claim 12, wherein the oxygen concentration sensor is configured to obtain the indication of the oxygen fraction of sampled inhalation gas in the first gas mixing chamber and the oxygen fraction of sampled exhalation gas in the second gas mixing chamber simultaneously.

14. The apparatus of claim 11, wherein the oxygen concentration sensor is configured to obtain the indication of the oxygen fraction of sampled inhalation gas in the first gas mixing chamber and the oxygen fraction of sampled exhalation gas in the second gas mixing chamber simultaneously.

15. The apparatus of claim 10, comprising:
a first sampling line communicating between an inhalation gas connector and the first gas mixing chamber; and
a second sampling line communicating between an exhalation gas connector and the second gas mixing chamber.

* * * * *